US010248885B2

(12) United States Patent
Nikolskiy et al.

(10) Patent No.: US 10,248,885 B2
(45) Date of Patent: Apr. 2, 2019

(54) METHOD FOR ENCODING OF ANATOMIC CURVES

(71) Applicant: James R. Glidewell Dental Ceramics, Inc., Newport Beach, CA (US)

(72) Inventors: Sergey Vladimirovich Nikolskiy, Coto de Caza, CA (US); Sergei Azernikov, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 1024 days.

(21) Appl. No.: 14/211,517

(22) Filed: Mar. 14, 2014

(65) Prior Publication Data

US 2014/0278278 A1 Sep. 18, 2014

Related U.S. Application Data

(60) Provisional application No. 61/799,110, filed on Mar. 15, 2013.

(51) Int. Cl.
*G06G 7/48* (2006.01)
*G06K 9/62* (2006.01)
*A61C 13/00* (2006.01)
*G06F 17/50* (2006.01)
*G16H 20/40* (2018.01)

(52) U.S. Cl.
CPC ........ *G06K 9/6215* (2013.01); *A61C 13/0003* (2013.01); *A61C 13/0004* (2013.01); *G06F 17/5009* (2013.01); *G16H 20/40* (2018.01)

(58) Field of Classification Search
USPC .......................................................... 703/6
See application file for complete search history.

(56) References Cited

U.S. PATENT DOCUMENTS

| 6,633,789 | B1 * | 10/2003 | Nikolskiy | ............. | G06F 19/321 433/2 |
| 7,428,481 | B2 * | 9/2008 | Nikolskiy | ............. | G06F 19/321 29/896.1 |
| 2004/0220691 | A1 * | 11/2004 | Hofmeister | ........ | A61C 13/0004 700/98 |
| 2007/0203599 | A1 * | 8/2007 | Shibata | ............. | A61C 13/0004 700/98 |

(Continued)

OTHER PUBLICATIONS

S. Wolthusen, et al., "Non-Forensic Odontological Biometrics," Fifth International Conference on Intelligent Information Hiding and Multimedia Signal Processing IIH-MSP'09, IEEE, Sep. 12, 2009, pp. 1105-1109.*

(Continued)

*Primary Examiner* — David Silver
(74) *Attorney, Agent, or Firm* — Dianne Burkhard

(57) ABSTRACT

A method for compact and descriptive representation of teeth shape (or other anatomic shapes) in terms of characteristic curves and its application to generation of automatic designs within dental CAD software or other software is provided. In an embodiment, a method includes capturing tooth shape by a network of characteristic curves (i.e. margin lines). In an embodiment, a method includes compactly encoding curves as strings, which then can be indexed and searched efficiently by similarity. In an embodiment, a method includes retrieving high quality crown design proposals from a case repository based on similarity of margin lines.

12 Claims, 4 Drawing Sheets

Automatic proposal generation workflow

(56) References Cited

U.S. PATENT DOCUMENTS

| | | | |
|---|---|---|---|
| 2007/0203600 A1* | 8/2007 | Shibata | A61C 13/0004 700/98 |
| 2009/0042167 A1* | 2/2009 | Van Der Zel | A61C 1/084 433/215 |
| 2010/0281370 A1 | 11/2010 | Rohaly et al. | |
| 2011/0213700 A1 | 9/2011 | Sant'Anselmo | |
| 2012/0139142 A1* | 6/2012 | Van Der Zel | A61C 13/0004 264/20 |
| 2012/0239177 A1 | 9/2012 | Taub et al. | |
| 2013/0226534 A1* | 8/2013 | Fisker | G06F 17/50 703/1 |
| 2014/0278279 A1 | 9/2014 | Azernikov et al. | |

OTHER PUBLICATIONS

R. Vaddi, et al., "Contour Detection Using Freeman Chain Code and Approximation Methods for the Real Time Object Detection," Asian Journal of Computer Science and Information Technology, vol. 1, No. 1, 2011, pp. 15-17.*

International Search Report for PCT/US2014/28754 dated Aug. 20, 2014.

Kiattisin, S et al. "Match of X-ray Teeth Films Using Image Processing Based on Special Features of Teeth", SICE Annual Conference, 2008. IEEE: Aug. 22, 2008; p. 97; col. 2, paragraph 2; a 98, cols. 1-2.

Brisbiesca, E. "3D-Curve Representation by Means of a Binary Chain Code", Mathematical and Computer Modeling 40.3(2004):285-295; 2004; p. 292, paragraph 2; p. 293, paragraph 1.

Cui, M , Femiani, J., Hu, J., Wondka, Razada A. "Curve Matching for Open 2D Curves", Pattern Recognition Letters 30 (2009): pp. 1-10.

Gumhold, S., Wang, X., Macleod R. "Feature Extraction From Point Clouds", Scientific Computing and Imaging Institute: pp. 1-13 Proceedings, 10th International Meshing Roundtable, Sandia National Laboratories, pp. 293-305, Oct. 7-10, 2001.

Wolfson, H. "On Curve Matching", Robotics Research Technical Report, Technical Report No. 256, Robotic Report No. 86 (Nov. 1986). New York University, Dept. of Computer Science, New York, New York 10012.

* cited by examiner

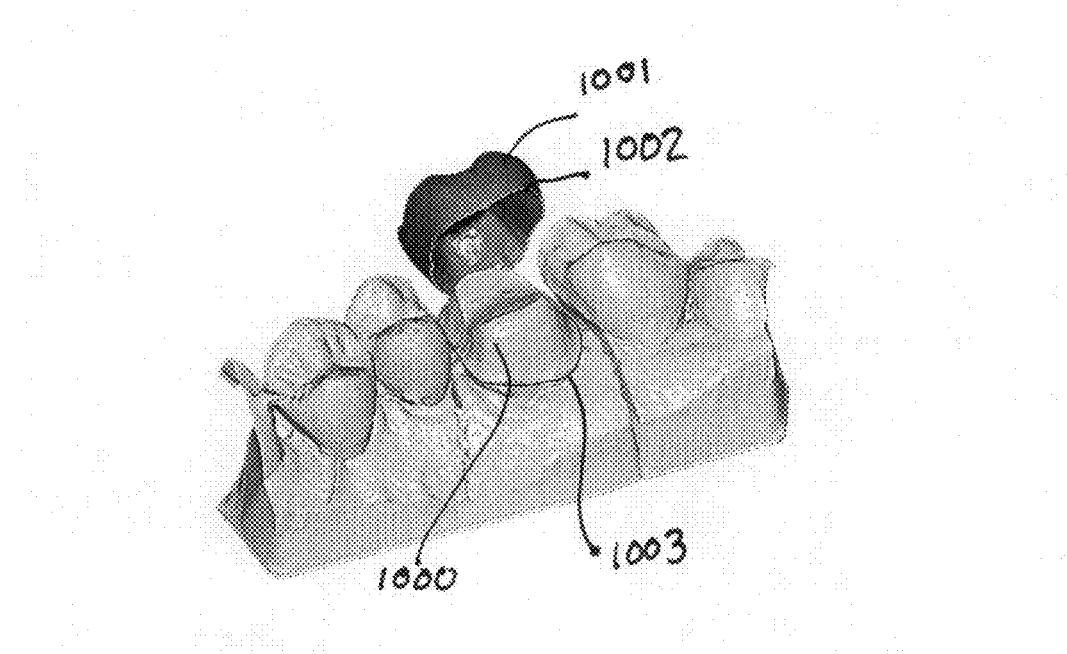
FIG. 1 - Margin lines marked on preparation and crown
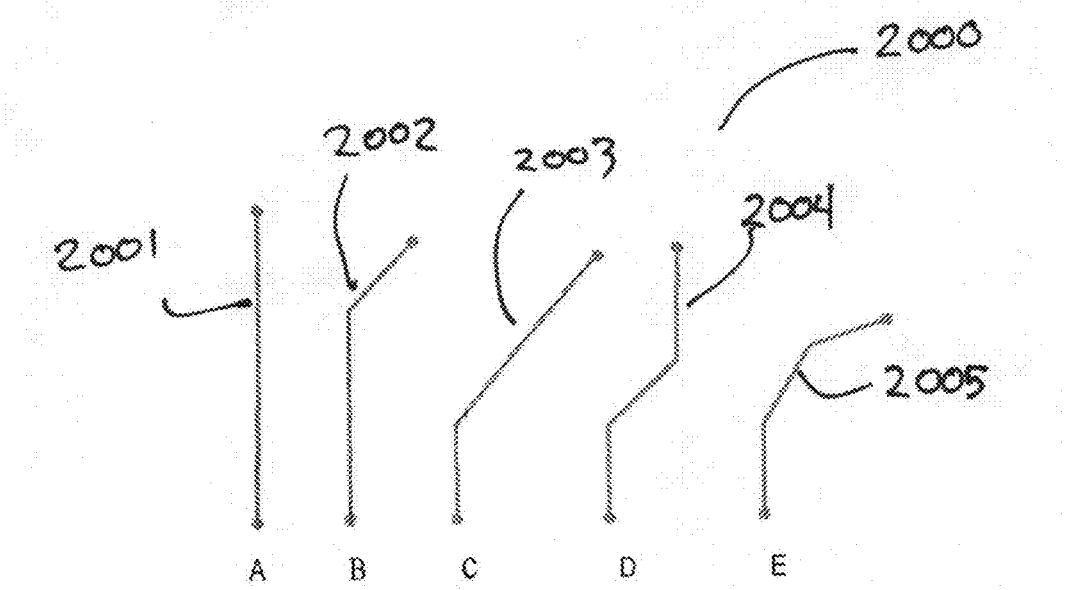
FIG. 2 - Curve encoding alphabet

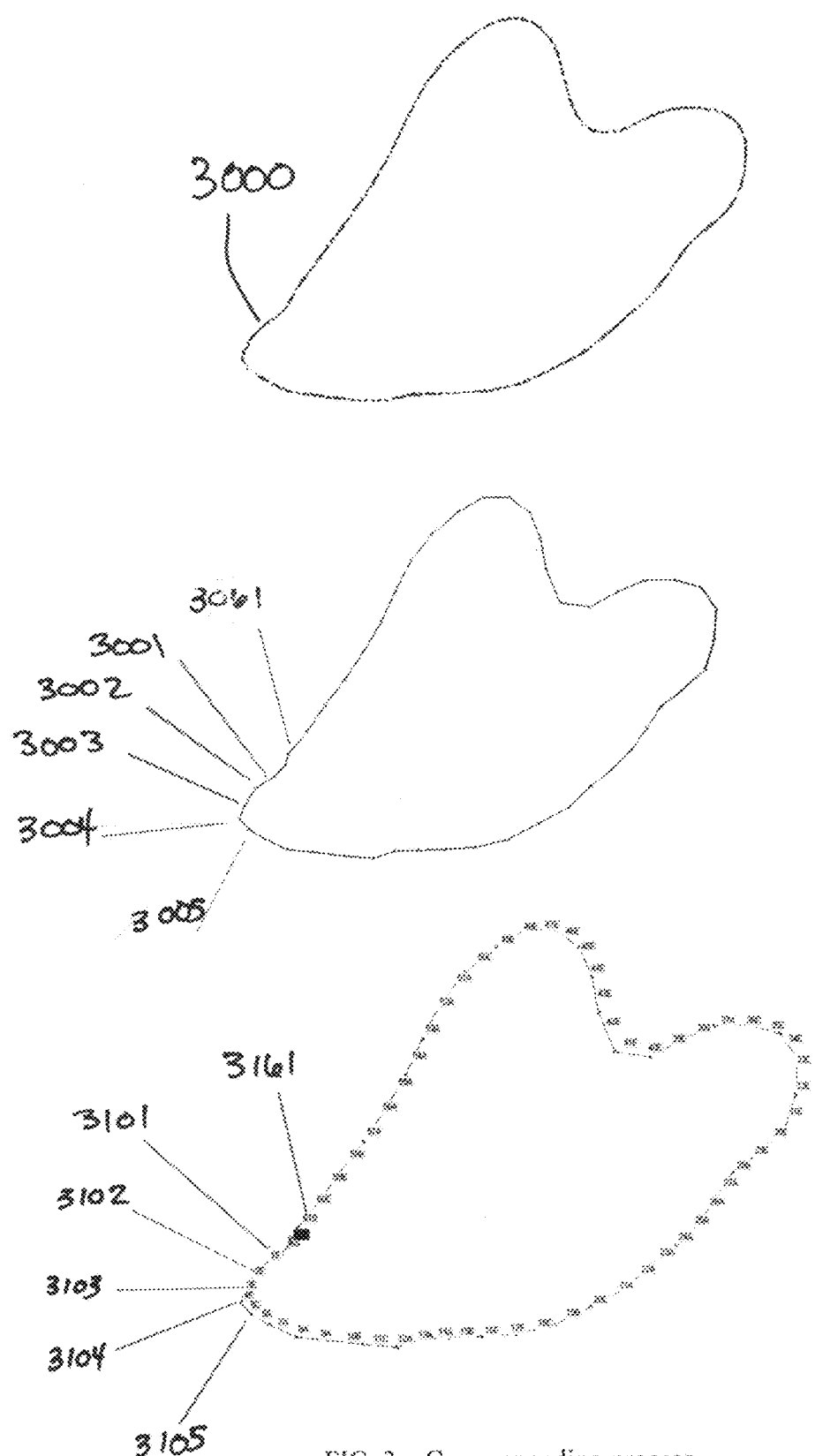
FIG. 3 – Curve encoding process

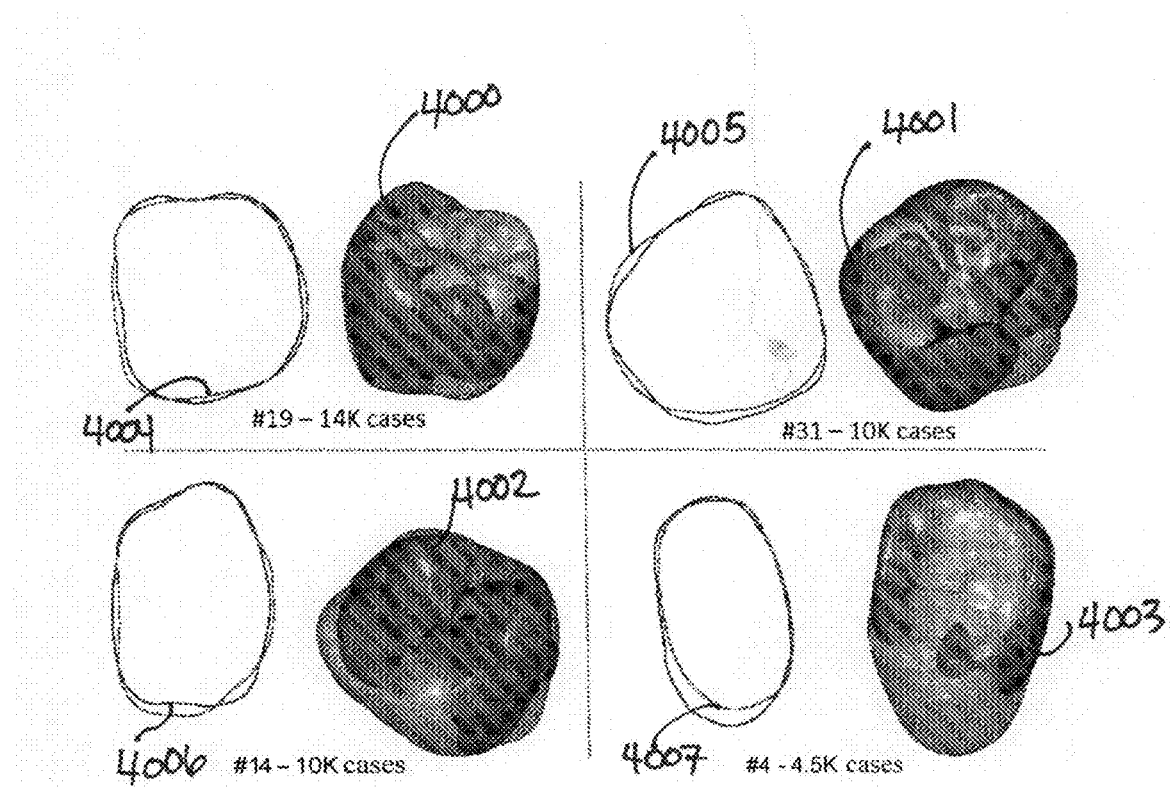
FIG. 4 - Database search results by margin line similarity

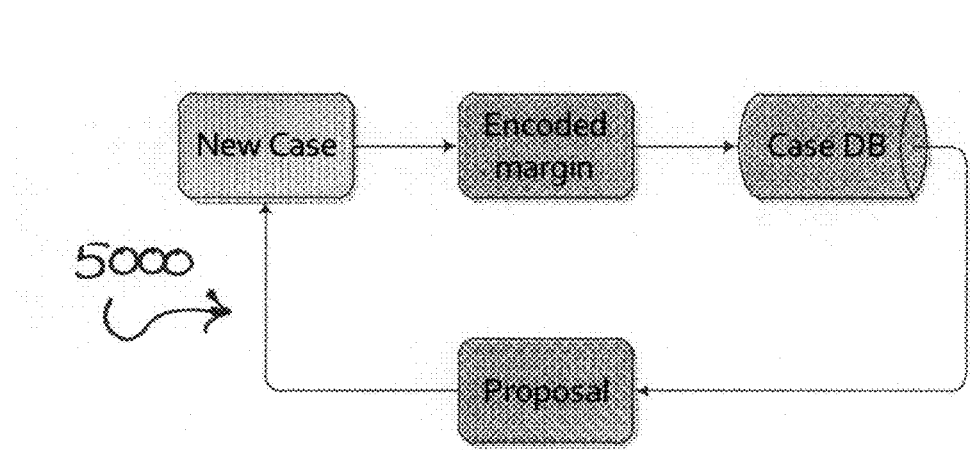
FIG. 5 - Automatic proposal generation workflow
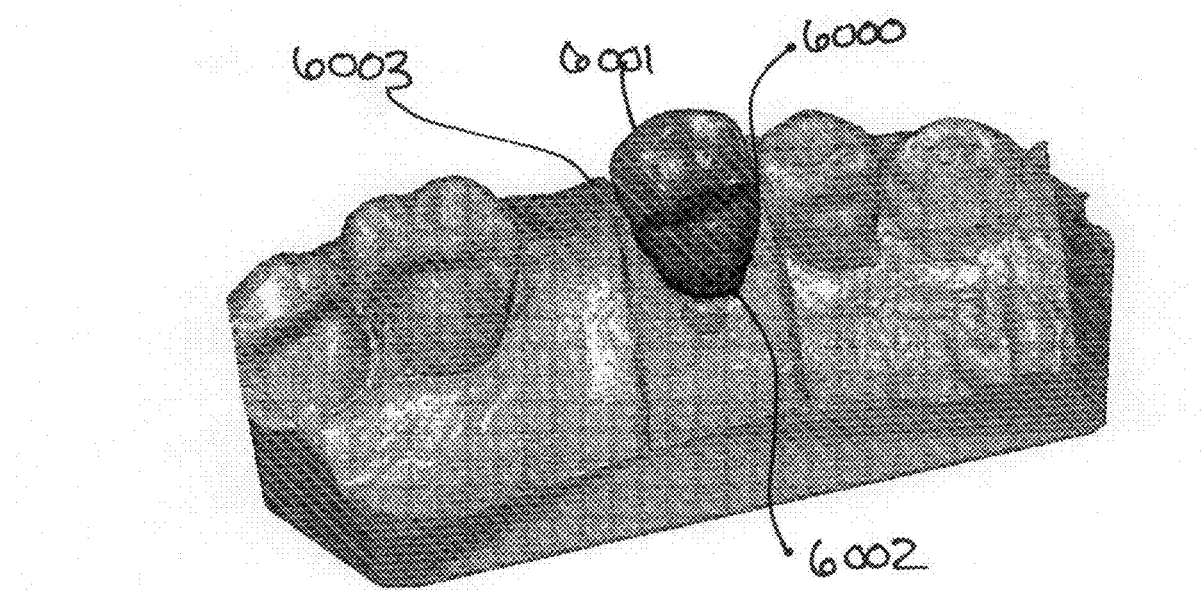
FIG. 6 – Automatically generated proposal

METHOD FOR ENCODING OF ANATOMIC CURVES

CROSS-REFERENCE TO RELATED APPLICATIONS

This application claims the benefit of U.S. Provisional Application Ser. No. 61/799,110, filed Mar. 15, 2013, the content of which application is hereby incorporated by reference herein.

FIELD

The present disclosure generally relates to methods for encoding of anatomic curves, and applications of such methods including applications to dental CAD automation.

BACKGROUND

The proposal generation currently in use with respect to dental applications is based on a single generic template. Due to the high anatomic variability, a large amount of deformation is required in order to produce the final tooth shape.

It would be desirable to have a method that would generate proposals which are much closer to the final shape.

SUMMARY

This disclosure provides a method for compact and descriptive representation of teeth shape (or other anatomic shapes) in terms of characteristic curves and its application to generation of automatic designs within dental CAD software or other software. In an embodiment, a tooth shape can be faithfully captured by a network of characteristic curves (i.e. margin lines). In an embodiment, curves can be compactly encoded as strings, which then can be indexed and searched efficiently by similarity. In an embodiment, high quality crown design proposals can be retrieved from the case repository based on similarity of margin lines.

In an embodiment, a method includes one or more of the following steps: (1) capturing tooth shape by a network of characteristic curves (i.e. margin lines); (2) compactly encoding curves as strings, which then can be indexed and searched efficiently by similarity; and (3) retrieving high quality crown design proposals from a case repository based on similarity of margin lines.

In an embodiment, a method includes: capturing tooth shape by a network of characteristic curves (i.e. margin lines); compactly encoding curves as strings, which can then by indexed and searched efficiently by similarity; and retrieving high quality crown design proposals from a case repository based on similarity of margin lines.

In an embodiment, a method is provided that includes leveraging from vast numbers of previously completed designs in order to generate proposals which are much closer to the final shape.

The present method includes searching for similar cases in the database and using the closest completed design as the proposal. It should be appreciated that such apparatus can be useful for many other applications including applications outside the dental domain, such as 3D search engines, real-time recognition and tracking of 3D objects and others.

BRIEF DESCRIPTION OF THE DRAWINGS

FIG. 1 shows an embodiment in which margin lines are marked on the preparation and the restoration crown.

FIG. 2 shows a curve encoding alphabet used in an embodiment of the method of the present disclosure.

FIG. 3 depicts an embodiment of a curve encoding process.

FIG. 4 shows an example of database search results by margin line similarity.

FIG. 5 depicts an embodiment of a method for automatic proposal generation.

FIG. 6 shows an embodiment of an automatically generated proposal.

While the above-identified drawings set forth presently disclosed embodiments, other embodiments are also contemplated, as noted in the detailed description. This disclosure presents illustrative embodiments by way of representation and not limitation. Numerous other modifications and embodiments can be devised by those skilled in the art which fall within the scope and spirit of the principles of the present disclosure.

DETAILED DESCRIPTION

Methods and systems for efficient encoding of anatomic curves, and application of such methods and systems to dental CAD automation are provided.

In an embodiment, a method includes one or more of the following steps: (1) capturing tooth shape by a network of characteristic curves (i.e. margin lines); (2) compactly encoding curves as strings, which then can be indexed and searched efficiently by similarity; and (3) retrieving high quality crown design proposals from a case repository based on similarity of margin lines.

Margin Line

Margin line is the area of contact between a preparation (1000) done by a dentist and the restoration crown (1001), or other prosthesis. Clear margin lines are very important to guarantee good fit of the crown. FIG. 1 shows margin lines (1003, 1002) marked on the preparation (1000) and the restoration crown (1001).

From Curves to Strings

Direct search in large repositories of general 3D curves is a computationally expensive task. One commonly used approach is adaptive sampling of the curve and working with resulting sparse polylines. However, dense sampling may be required to represent high curvatures and/or small features. In an embodiment of the present disclosure, curve shape is encoded using a pre-defined alphabet (2000) shown in FIG. 2. Each letter (2001, 2002, 2003, 2004, 2005) in the alphabet represents certain local behavior of the discretized curve.

FIG. 3 depicts an embodiment of a curve encoding process. First, the given parametric curve (3000) may be sampled (3001, 3002, 3003, 3004, 3005, 3061) with constant density (for example, 0.5 mm). Next, a label (3101) (e.g., 1E) is associated with each sample point (e.g., 3001) based on the alphabet described above. Linked together, these labels (3101, 3102, 3103, 3104, 3105, 3161) constitute a chain code. Previously proposed encoding schemes were based on orthogonal direction change. These schemes, however, are not suitable in many cases where curves are smooth and do not contain sharp turns, as with the dental margin lines which were mentioned above, for example.

String Similarity Measure

Once curves are encoded as strings, it is possible to apply well-established methods for string search and comparison. In this work, Levenshtein distance is used to measure similarities between the chain code strings. Roughly speaking, this measure indicates how many edits are required to apply on one string to make it equal to another. This metric proved to be effective in many areas, including spell checkers, search engines and DNA matching. Levenshtein distance can be used to define the similarity measure between two strings a and b as follows:

$$s(a, b) = 1 - \frac{lev(a, b)}{\max(\text{length}(a), \text{length}(b))},$$

where lev(a, b) is the Levenshtein distance between string a and b, and length (a) is a number of characters in string a. As indicated, similarity will be equal to 1 only when two strings are identical.

In order to test the proposed similarity measure, databases of various tooth numbers were created. Random crown was picked and the most similar but different case was extracted from the database. As can be seen in FIG. 4, found cases (4000, 4001, 4002, 4003) have similar margin lines (4004, 4005, 4006, 4007) and overall shapes. Based on these findings, an automatic proposal generation mechanism was developed.

Automatic Proposal Generation

FIG. 5 depicts an embodiment of a method of proposal generation (5000). FIG. 5 shows the automatic proposal generation workflow. In FIG. 6, automatically generated proposal (6001) for tooth #4 (UNI) (6000) is presented. The only information that was utilized in order to generate this proposal was the margin line (6002) on the preparation scan (6003). Since the search for proposal is based on margin line similarity, good fit is naturally achieved. On the other hand, the height of the crown may require modification, which is rather straightforward.

In addition to dental applications, the presently disclosed methods may have applications in areas other than dentistry. Efficient shape encoding and search may be utilized in systems such as 3D search engines (e.g., Google 3D Warehouse™), real-time tracking systems (e.g., Microsoft Kinect™) and others.

It will be appreciated that several of the above-disclosed and other features and functions, or alternatives thereof, may be desirably combined into many other different methods, systems or applications. Various alternatives, modifications, variations, or improvements therein may be subsequently made by those skilled in the art which fall within the scope and spirit of the principles of the present disclosure.

We claim:

1. A method for automatic generation of a design proposal for a dental restoration prosthesis to be used as a tooth restoration for a patient comprising the steps of:
   in a computing system,
   a. identifying and sampling a characteristic curve of a tooth preparation of the patient to be restored with the dental restoration prosthesis, at a plurality of sample points;
   b. encoding the characteristic curve of the tooth preparation of the patient as a string by a curve encoding process;
   c. searching a database of cases of previously completed tooth restoration designs, each case having
      i. a dental restoration prosthesis design, and
      ii. a string encoding a characteristic curve of the dental restoration prosthesis design,
   d. measuring similarities and defining a plurality of string similarity measures between the string of the tooth preparation and the strings of the database;
   e. obtaining one of the dental restoration prosthesis designs as the design proposal for the dental restoration prosthesis for the tooth preparation based on the string similarity measures; and
   f. using the design proposal as a design for the dental restoration prosthesis.

2. The method of claim 1, wherein the characteristic curve for each the tooth preparation and the characteristic curve of the dental restoration prosthesis design is a margin line.

3. The method of claim 2, wherein the method comprises searching the database for string similarity measures between a margin line of the tooth preparation to be restored and the margin lines of completed tooth restoration designs.

4. The method of claim 1, wherein the database is a case repository of previously completed restoration crown designs, and the method comprises obtaining restoration crown design proposals from the case repository based on the string similarity measures of margin lines of the restoration crown design proposals and the tooth preparation.

5. The method of claim 1, comprising sampling the characteristic curve of the tooth preparation at a sample point and associating a label with each sample point of the characteristic curve.

6. The method of claim 5, wherein the labels of each sample point, linked together, constitute a chain code.

7. The method of claim 5, wherein the label is based on a pre-defined curve-encoding alphabet having letters, and each letter represents a behavior of the characteristic curve.

8. The method of claim 1, comprising sampling the curve at constant density.

9. The method of claim 1, wherein a Levenshtein distance is used to define a string similarity measure between the string of the tooth preparation and the string of each tooth restoration design case.

10. The method of claim 1, wherein the design proposal is for a restoration crown.

11. The method of claim 1, comprising retrieving a plurality of completed design proposals from the database, comparing the string similarity measures, and using the completed design proposal that has the greatest string similarity measure for a restoration prosthesis.

12. A method for generating design proposals for a restoration crown to be used as a tooth restoration for a patient from a case repository comprising the steps of:
   in a computing system,
   a. encoding a margin line of a tooth preparation of the patient as a tooth preparation string with a curve-encoding alphabet by
      i. sampling the margin line, and
      ii. associating a letter selected from the curve-encoding alphabet with each sample, wherein the letter represents a certain local behavior; and
      iii. linking the letters together to form the preparation string,
   b. searching a case repository of previously completed restoration crown designs in which a margin of each previously completed restoration crown design has been encoded as a string;
   c. obtaining string similarity measures by measuring similarities between the tooth preparation string and each restoration crown design string of the previously completed restoration crown designs of the case repository;
   d. obtaining a plurality of completed restoration crown designs as design proposals for the restoration crown for the tooth preparation from the case repository based on the string similarity measures of the tooth preparation string and each restoration crown design string;

e. selecting one of the completed restoration crown designs from the plurality of completed restoration design proposals for the restoration crown design for the tooth restoration.

\* \* \* \* \*